United States Patent [19]

Sweeney

[11] 4,182,320

[45] Jan. 8, 1980

[54] DISPOSABLE PROTECTIVE SLEEVE, HAVING A PNEUMATIC ACTION, FOR A RIGID SPLINT BOARD OR THE LIKE

[75] Inventor: Kevin M. Sweeney, Woodstock, N.Y.

[73] Assignee: Simulaids, Inc., Woodstock, N.Y.

[21] Appl. No.: 880,606

[22] Filed: Feb. 23, 1978

[51] Int. Cl.$^2$ ............................................. A61F 5/04
[52] U.S. Cl. ........................... 128/89 R; 128/DIG. 20
[58] Field of Search .......... 128/89 R, 87 R, DIG. 20, 128/DIG. 6

[56] References Cited

U.S. PATENT DOCUMENTS

| 3,242,923 | 3/1966 | Jacoby, Sr. ................. 128/DIG. 20 |
| 3,811,434 | 5/1974 | Jacobson et al. ................. 128/89 R |

FOREIGN PATENT DOCUMENTS 1350754 12/1963 France ............................. 128/DIG. 20

*Primary Examiner*—John D. Yasko
*Attorney, Agent, or Firm*—Mandeville and Schweitzer

[57] ABSTRACT

Disclosed herein is a disposable, foldable and inflatable protective sleeve for a conventional, re-usable, rigid splint board. The sleeve comprises three juxtaposed sheets of thermoplastic material fastened together to form two expansible pockets. One of the pockets is provided with an opening for insertion of the rigid splint board to provide a sanitary splint to support, in an immobile position, the limb of a patient. A valve is associated with the other of the pockets so that it may be inflated to provide a yieldable, cushion-like surface between the splint and the limb for maximum patient comfort. Advantageously, the inflated pocket will apply a stretching force to the first pocket to retain the rigid splint board securely therein. Prior to use, the protective sleeve is compactly foldable for convenient, sanitary storage. The disclosed structure affords easy insertion of a conventional splint board and subsequent inflation for a highly effective limb support. After use, the sleeve is disposable.

6 Claims, 6 Drawing Figures

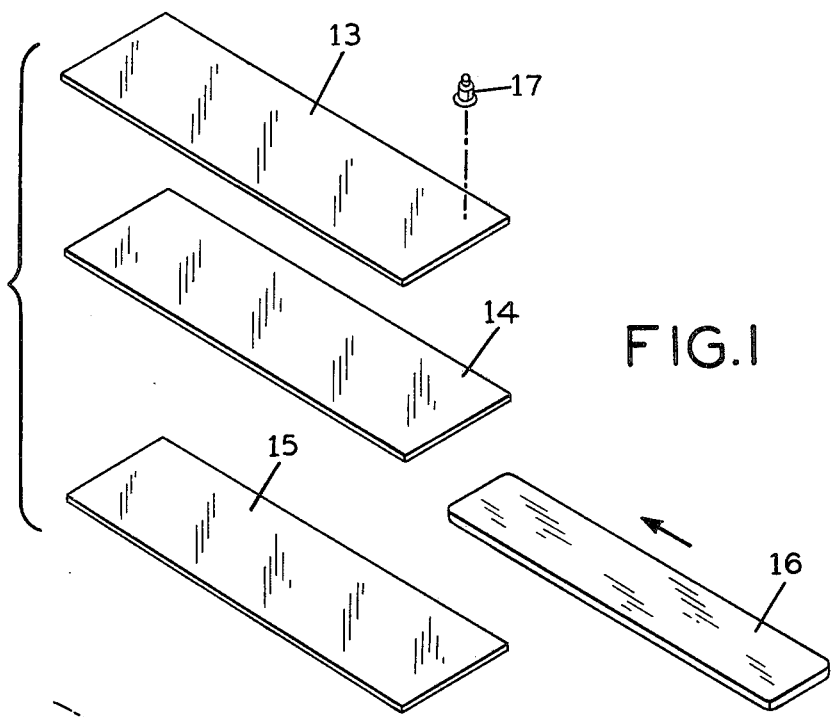
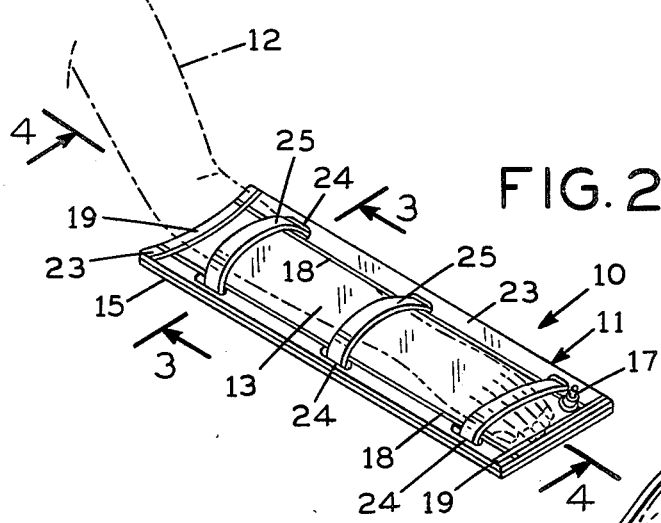
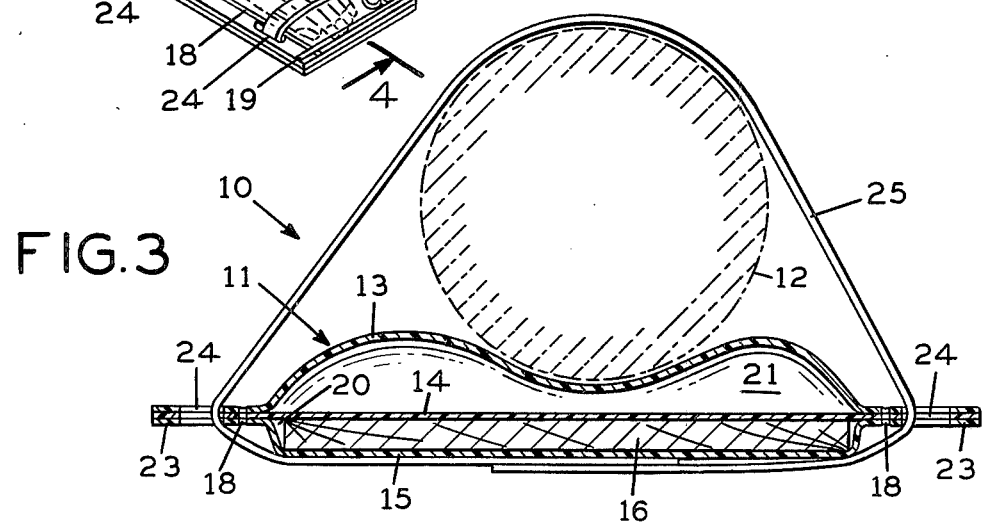

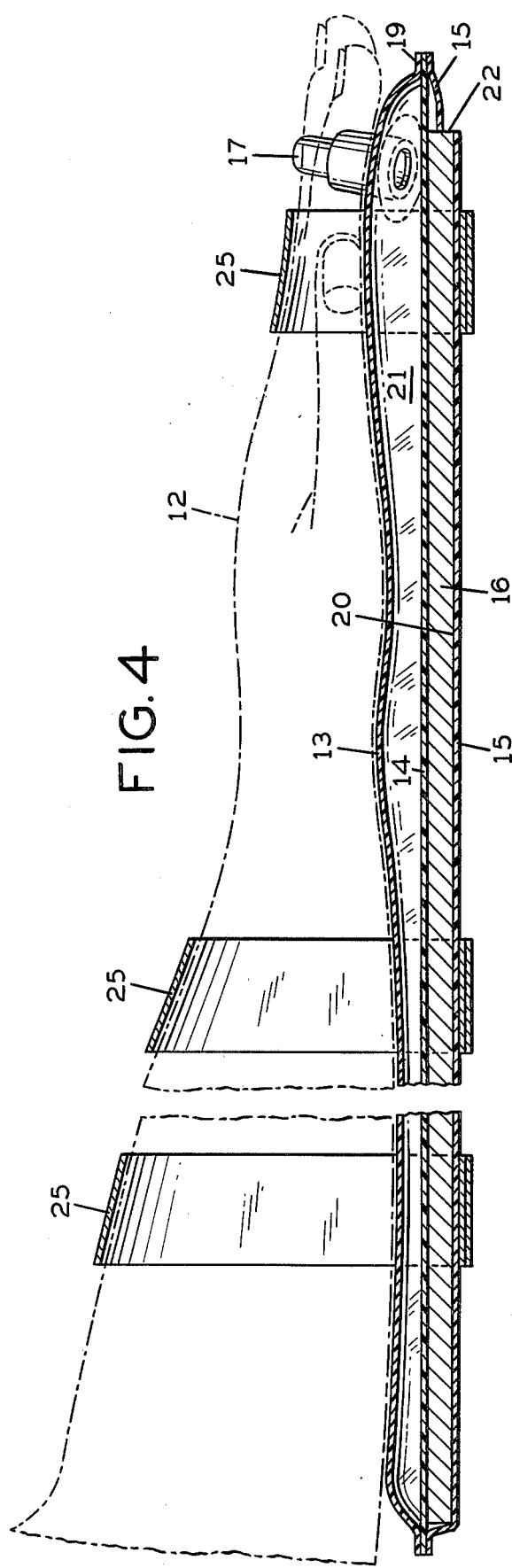
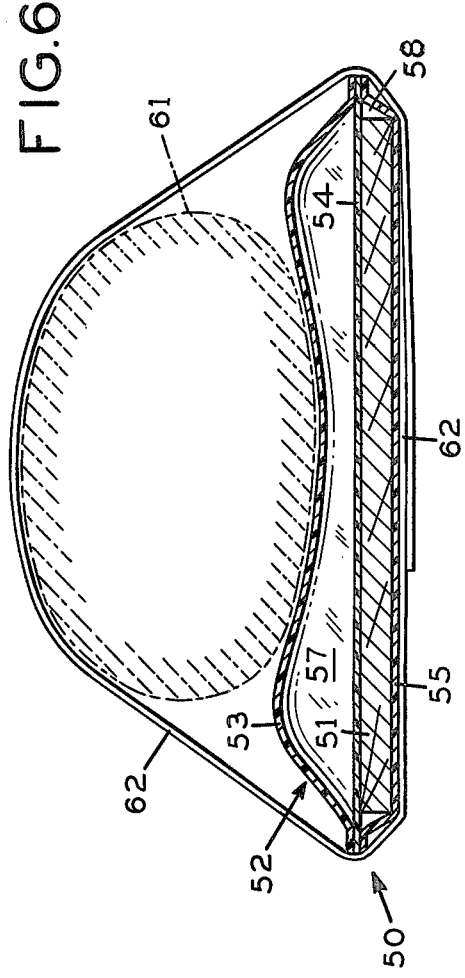
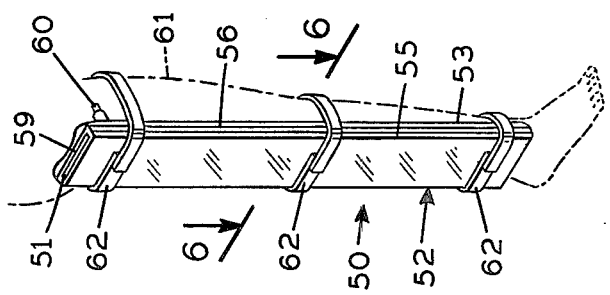

DISPOSABLE PROTECTIVE SLEEVE, HAVING A PNEUMATIC ACTION, FOR A RIGID SPLINT BOARD OR THE LIKE

BACKGROUND AND SUMMARY OF THE INVENTION

The present invention is related, in general, to cushioned splints for bracing and supporting the limbs of a patient, and more particularly is directed to a disposable, protective sleeve, having a pneumatic action for a rigid re-usable splint board.

In the proper care of an injured limb or for the support of a limb during intravenous feeding or the like, it is highly desirable to utilize a rigid support board to maintain the limb in an immobile, secure position. To this end, many devices have been proposed to provide splints with cushioning for the patient's comfort. Moreover, some of the prior devices include disposable components. Representative, but by no means exhaustive of such prior art devices, are the splints disclosed in the McInnerny U.S. Pat. No. 2,763,264; Bird U.S. Pat. No. 2,953,131; Schwartz U.S. Pat. No. 3,059,636; Cullen et al. U.S. Pat. No. 3,075,522; Jacoby, Sr. U.S. Pat. No. 3,242,923; and Eisenberg U.S. Pat. No. 3,556,092. Each of the above-cited prior art proposals provides a splint for supporting a patient's limb in a firm position, while maintaining immobility for the proper care and treatment of the patient. However, these devices have not always proven to be entirely satisfactory for use in their intended application inasmuch as they lack optimum features for maximum convenience in storing, handling and mounting of the splint.

It is a primary objective of the present invention to provide a new and improved disposable pneumatic action sleeve for use in association with re-usable splint boards. The pneumatic sleeve disclosed herein is very simple and inexpensive to manufacture, it is foldable for easy storage and is straightforward in design and operation to provide fast and effective use as a protective, cushioned sleeve for a limb support. Moreover, the pneumatic action of the diposable sleeve provides the patient with a comfortable fit when mounted in a fully assembled splint. More particularly, the disposable sleeve of the invention comprises three rectangular sheets of foldable thermoplastic material, each sheet being formed generally to be slightly in excess of the length and width dimensions of a standard rigid splint board. The sheets are arranged in a juxtaposed relation, and are fastened together by a heat seal along the outer perimeter of the sheets. This forms a foldable sleeve of two outer sheets enclosing the third intermediate sheet. The sheets are arranged, configured and fastened in such a manner whereby the intermediate sheet forms an air-tight, expansible pocket with each of the outer two sheets. In accordance with the invention, a transverse slit or opening is formed in one of the outer sheets at one end thereof. The opening provides access to the interior of one of the pockets whereby a commercially available re-usable rigid splint board may be inserted into the pocket to form a rigid, disposable sleeve. The sleeve provides a sanitary, protective covering for the re-usable splint board. A valve means is associated with the other of the outer sheets. The valve means is operable to inflate the pocket defined by the other outer sheet and intermediate sheet. The inflated pocket provides a pillow-like cushion for the patient's limb. Moreover, the expanded pocket applies a stretching force to the first outer sheet to securely retain the splint board within its pocket.

To advantage, the heat seal may be formed in a spaced relation to the outer edges of the sheets to provide a pair of wing flaps at the perimeter of the inflated splint. A plurality of slots are formed through the flaps to accommodate straps to attach the splint to the patient's arm. Of course, the disposable, pneumatic action sleeve of the invention may be proportioned for use in supporting either a leg or an arm of the patient, and may be arranged to be attached to the limb in any suitable manner, for example, straps applied around the splint and limb.

For a better understanding of these and other advantages and features of the present invention, reference should be made to the following detailed description of preferred embodiments of the invention and to the accompanying drawings.

BRIEF DESCRIPTION OF THE DRAWINGS

FIG. 1 is an exploded, perspective view of the principal components of the disposable sleeve of the present invention in unassembled form and the rigid splint board used therewith.

FIG. 2 is a perspective view of a splint board arranged on the arm of a patient and enclosed within the disposable sleeve of the present invention.

FIG. 3 is an end cross-sectional view of the splint and sleeve taken generally along the line 3—3 of FIG. 2.

FIG. 4 is a partial side cross-sectional view of the splint and sleeve taken generally along line 4—4 of FIG. 2.

FIG. 5 is a perspective view of a splint board arranged on the leg of a patient and enclosed within a disposable sleeve of the present invention.

FIG. 6 is an end cross-sectional view of the splint and sleeve taken generally along line 6—6 of FIG. 5.

DETAILED DESCRIPTION OF PREFERRED EMBODIMENTS OF THE INVENTION

Referring now to the drawings, FIG. 2 illustrates a rigid splint 10, strapped to the arm 12 of a patient to hold the arm in a firm, immobile position for proper care and treatment. In accordance with the invention, the splint 10 is 18"×3½"×3/16" and provided with an inflatable, disposable sleeve 11 which is advantageously manufactured from three foldable sheets 13,14,15 of thermoplastic material such as PVC. The sheets 13,14,15 are cut generally to be slightly in excess of the width and length dimensions of the splint. As depicted in FIG. 1, the sheets 13,14,15 are aligned in a parallel, spaced relation and thereafter juxtaposed whereby the sheet 14 is placed between the sheets 13,15. The sheets 13,14,15 are then fastened together, as for example by heat seals 18 spaced parallel to the side edges of the sheets 13,14,15 and 19, at the ends of the sheets 13,14,15. In the preferred embodiment, the heat seals are approximately ⅛" wide. The above-described stacked and sealed sheet configuration provides the sleeve 11, including a first pocket 20 defined by the sealed sheets 14,15 and a second pocket 21 defined by the sealed sheets 13,14 which are clearly illustrated in FIGS. 3 and 4. The heat seals 18,19 form air-tight pockets 20,21. The sleeve 11 is ideally suited to receive all standard re-usable, rigid splint boards 16.

An inexpensive valve 17, for example, a plastic two-way "Roberts Valve" sold by the Halkey-Roberts Company of New Jersey is attached to the sheet 13. In this manner, the pocket 21 is inflatable. As can be seen in FIG. 4, a transverse slit 22 is formed in sheet 15 to provide an opening for convenient insertion of the splint board 16 into the pocket 20. After insertion of the board 16, the pocket 21 may be inflated by operation of the valve 17 whereby the patient's arm 12 will rest on a pillow-like cushion for maximum comfort. Inflation of the pocket 21 will tend to stretch the sheet 15 against the splint board 16 to secure the board 16 within the pocket 20. Thus, the splint board 16 may be re-used each time with a new sleeve 11. The board 16 will always be enclosed by an outer protective sanitary sleeve.

Inasmuch as the sleeve 11 comprises flexible sheets, it may be folded to a small size for storage in a sanitary package. When needed, the sleeve 11 is simply unfolded, the board 16 is inserted into the pocket 20 through the slit 22 and the pocket 21 is inflated to complete the splint 10. To advantage, the heat seals 18 are formed spaced from the side of the sheets 13,14,15 to provide longitudinally extending wing flaps 23 on either side of the sleeve 11. A plurality of slots 24 are cut into flaps 23 so that supporting straps 25 may be laced through complementary slots 24 on either side of the sleeve 11 to attach the splint 10 to the patient's arm 12. The straps 25 may be provided with Velcro ® fasteners at the ends thereof so that when the ends are placed in an overlapping relation, the Velcro ® material will engage to secure the straps 25.

Referring now to FIGS. 5 and 6, there is illustrated a splint 50 designed to support a patient's leg 61. The splint 50 comprises a commercially available rigid plywood splint board 51 enclosed within a disposable sleeve 52 built in accordance with the principles of the present invention. As in the prior embodiment, the sleeve 52 comprises three sheets 53,54,55 of juxtaposed thermoplastic material fastened together by heat seals 56 formed at the perimeter of the sheets 53,54,55. This arrangement of fastened sheets defines a first expansible pocket 57 between the sealed sheets 53,54 and a second expansible pocket 58 between the sealed sheets 54,55. A transverse slit 59 is cut in the sheet 55 whereby the splint board 51 may be inserted into the pocket 58. A valve 60 is mounted on the sheet 54 such that the pocket 57 may be inflated after insertion of the splint board 51 to provide a yieldable cushion. The splint 50 is placed against the injured leg 61 as illustrated in FIG. 5 and secured thereto by a plurality of straps 62 wrapped around the leg 61 and splint 50. The straps 62 may be provided with Velcro ® material at the ends thereof for fastening. Of course, any other suitable fastening means, such as buckles, may be utilized to secure the straps 62.

The present invention provides a highly effective sleeve for standard rigid splint boards commonly used in the care and treatment of patients. The sleeve is simply and inexpensively manufactured by cutting and stacking three sheets of thermoplastic material and thereafter sealing the sheets to one another by a simple heat sealing step to provide two air-tight pockets. One of the pockets is utilized to retain the plywood splint board and the other of said pockets is inflatable to provide a pillow-like cushion for maximum patient comfort. Prior to use, the protective sleeve is foldable for easy storage and after use the sleeve is disposable. Thus, the present invention provides a straightforward protective sleeve which permits the maintenance of the highest possible sanitary conditions and most efficiency in cost, storage and use.

It should be understood, of course, that the preferred embodiments of the protective sleeve illustrated and described herein are representative only, and as understood by those skilled in the arts, certain changes may be made therein without departing from the scope of the invention. Accordingly, reference should be made to the following appended claims to determine the full scope of the invention.

I claim:

1. A foldable, disposable, inflatable protective sleeve for use in association with a re-usable, rigid splint board, which comprises
    (a) three rectangular sheets of thermoplastic material each being formed to be slightly in excess of the rigid splint board width and length dimensions and being arranged and configured in juxtaposed layers comprising two outer sheets and one intermediate sheet,
    (b) fastening means to form an air-tight seal between the three juxtaposed sheets at the peripheral portions thereof,
    (c) a first expansible pocket defined by the air-tight seal, one of said outer sheets and the intermediate sheet,
    (d) a second expansible pocket defined by the air-tight seal, the other of said outer sheets and the intermediate sheet,
    (e) an access slot being formed in said first pocket,
    (f) said rigid splint board being insertable into the first pocket through said access slot, and
    (g) selectively operable valve means associated with said second pocket whereby pressure fluid may be admitted to said second pocket, thereby inflating the second pocket to provide a yieldable, pillow-like supporting surface over the inserted rigid splint board.

2. The protective sleeve according to claim 1, further characterized by
    (a) said fastening means comprising a heat seal formed at the outer perimeter of the three juxtaposed thermoplastic sheets.

3. The protective sleeve according to claim 1, further characterized by
    (a) said valve means comprising a plastic two-way valve mounted to the outer sheet defining said second pocket.

4. The protective sleeve according to claim 1, further characterized by
    (a) said sheets being formed to have dimensions slightly in excess of the width and length dimensions of a splint board arranged to support a human arm.

5. The protective sleeve according to claim 1, further characterized by
    (a) said sheets being formed to have dimensions slightly in excess of the width and length dimensions of a splint board arranged to support a human leg.

6. A foldable, disposable, inflatable protective sleeve for a re-usable, rigid splint board, which comprises
    (a) three rectangular sheets of thermoplastic material each being formed to be slightly in excess of the rigid splint board width and length dimensions and being arranged and configured in juxtaposed layers comprising two outer sheets and one intermediate sheet, (b) fastening means to form an air-tight seal between the three juxtaposed sheets at the peripheral portions thereof, (c) a first expansible pocket defined by the air-tight seal, one of said outer sheets and the intermediate sheet, (d) a second expansible pocket defined by the air-tight seal, the other of said outer sheets and the intermediate sheet, (e) an access slot being formed in said first pocket for insertion of said rigid splint board, and (f) selectively operable valve means associated with said second pocket whereby pressure fluid may be admitted to said second pocket, thereby inflating the second pocket to provide a yieldable supporting surface, (g) said fastening means comprising a heat seal formed at the outer perimeter of the three juxtaposed thermoplastic sheets, (h) said heat seal being formed in a spaced, parallel relation to the side edges of the sheets to form wing flap portions along the sides of said protective sleeve, (i) a plurality of slot openings formed in said wing flaps, and (j) a plurality of supporting straps whereby after insertion of said rigid splint board into said first pocket and inflation of said second pocket, said straps may be laced through said slot openings to attach said protective sleeve and rigid splint board to a patient's limb.

* * * * *